United States Patent [19]

Bugaut et al.

[11] 4,330,292
[45] May 18, 1982

[54] DYEING COMPOSITIONS FOR KERATIN FIBRES CONTAINING META-PHENYLENEDIAMINES

[75] Inventors: Andrée Bugaut, Boulogne; Jean-Jacques M. Vandenbossche; Majdi M. Shahin, both of Aulnay-sous-Bois; Grégoire Kalopissis, Neuilly-sur-Seine, all of France

[73] Assignee: L'Oreal, Paris, France

[21] Appl. No.: 215,531

[22] Filed: Dec. 11, 1980

[30] Foreign Application Priority Data

Jan. 9, 1980 [FR] France .................... 80 00390

[51] Int. Cl.³ .................... A61K 7/13; C07C 93/14
[52] U.S. Cl. .................... 8/411; 8/406; 8/409; 8/416
[58] Field of Search .................... 8/406, 409, 411, 416

[56] References Cited

U.S. PATENT DOCUMENTS

| | | | |
|---|---|---|---|
| 4,125,367 | 11/1978 | Busaut et al. | 8/407 |
| 4,152,112 | 5/1979 | Busaut et al. | 8/410 |
| 4,259,261 | 3/1981 | Busaut et al. | 564/220 |

FOREIGN PATENT DOCUMENTS 882925 10/1980 Belgium .
52-36635 3/1977 Japan .
2025958 1/1980 United Kingdom .

*Primary Examiner*—A. Lionel Clingman
*Attorney, Agent, or Firm*—Cushman, Darby & Cushman

[57] ABSTRACT

The invention resides in the use of the compounds having the formula given below, or an acid salt thereof, as couplers in dyeing compositions for keratin fibres which contain an oxidation base:

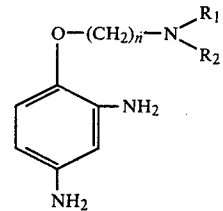

in which formula n is equal to 2, 3 or 4 and $R_1$ and $R_2$ are identical or different and represent an alkyl group having from 1 to 4 carbon atoms.

25 Claims, No Drawings

DYEING COMPOSITIONS FOR KERATIN FIBRES CONTAINING META-PHENYLENEDIAMINES

The present invention relates to dyeing compositions for keratin fibres, using meta-phenylenediamine compounds.

In the field of dyeing keratin fibres, hair or fur, meta-phenylenediamines play an important role which has been known for a long time; they form part of the class of compounds commonly referred to as "couplers". Couplers, in association with oxidation bases, such as para-phenylenediamines or para-aminophenols, give rise, in an oxidising alkaline medium, to coloured indamines, indoanilines or indophenols.

The association of meta-phenylenediamines with para-phenylenediamines, in an oxidising alkaline medium, gives rise to indamines which are capable of imparting very strong blue colourations to keratin fibres. Meta-phenylenediamines associated with para-aminophenols, in an oxidising alkaline medium, give indoanilines which impart, to keratin fibres, red colourations containing more or less purple. However, in practice, this category of couplers is limited to a very restricted number of compounds. This very restricted number is explained by the fact that, for hair dyeing, it is only possible to single out, on the one hand, those compounds which are harmless and, on the other hand, those compounds which make it possible to obtain dyes of good quality, that is to say dyes which do not change with time under the action of light, adverse weather conditions or washing.

French Pat. No. 2,455,030, filed on Apr. 26, 1979, describes meta-phenylenediamines which constitute a valuable category of couplers which can be used in dyeing compositions. The present invention provides a further category of meta-phenylenediamines, these having the formula (I) indicated below, and making it possible to obtain valuable results when they are used as couplers in the presence of oxidation bases, such as para-phenylenediamines or para-aminophenols; the dyes thus obtained possess a very good resistance to shampoos.

The present invention provides a dyeing composition for keratin fibres, and in particular for hair, the said composition containing, in a cosmetic carrier, at least one oxidation base and being characterised in that it contains, as the coupler, at least one meta-phenylenediamine of the formula (I):

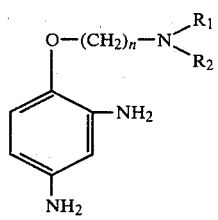

in which formula n is equal to 2, 3, or 4 and $R_1$ and $R_2$, which are identical or different, represent an alkyl group having from 1 to 4 carbon atoms, or at least one corresponding salt with an acid.

The meta-phenylenediamines of the formula (I), with an extranuclear amine, can be incorporated into dyeing compositions with oxidation bases including:

A. the para-phenylenediamines of the general formula:

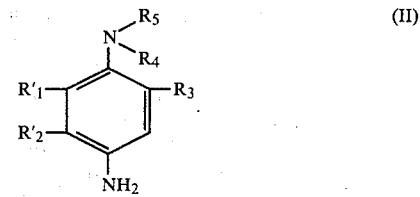

or the corresponding acid salts, in which formula $R'_1$, $R'_2$ and $R_3$ are identical or different and represent a hydrogen atom, an alkyl radical having from 1 to 4 carbon atoms, an alkoxy radical having 1 or 2 carbon atoms, or a halogen atom, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamylalkyl, alkylsulphonamidoalkyl, acetylaminoalkyl, ureidoalkyl, carbethoxyaminoalkyl, aminoalkyl, monoalkylaminoalkyl, dialkylaminoalkyl, piperidinoalkyl or morpholinoalkyl radical, the alkyl groups in $R_4$ and $R_5$ having from 1 to 4 carbon atoms, or alternatively $R_4$ and $R_5$ form, together with the nitrogen atom to which they are attached, a piperidino or morpholino group, with the proviso that $R'_1$ and $R_3$ represent a hydrogen atom if $R_4$ and $R_5$ do not represent a hydrogen atom; or B. the para-aminophenols of the general formula:

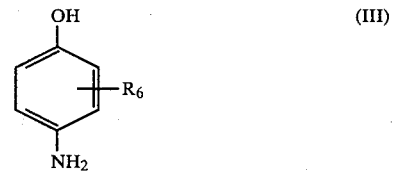

or the corresponding acid salts, in which formula $R_6$ represents a hydrogen atom, an alkyl radical containing from 1 to 4 carbon atoms, or a halogen atom, such as chlorine or bromine; or C. heterocyclic bases, such as 2,5-diaminopyridine, 3-methyl-7-aminobenzomorpholine and 5-aminoindole.

It has been found that the use of the meta-phenylenediamines of the formula (I) with para-phenylenediamines and/or para-aminophenols makes it possible to obtain dyeing compositions which impart, to the hair, shades of good quality which do not change on washing.

Amongst the compounds of the formula (I) (or their corresponding acid salts), it has been found that particularly valuable results can be obtained with 2,4-diaminophenyl β-diethylaminoethyl ether trihydrochloride.

The dyeing compositions forming the subject of the invention can contain, in addition to the coupler (or couplers) of the formula (I) and the associated oxidation base (or bases), other products and, in particularly the following, singly or in combination:

(1) other known couplers, for example resorcinol, pyrocatechol, 2-methylresorcinol, 2-ethylresorcinol, meta-aminophenol, 2-methyl-5-aminophenol, 2-methyl-5-N-(β-hydroxyethyl)-aminophenol, 6-hydroxybenzomorpholine, 2,6-dimethyl-3-acetylaminophenol, 2-methyl-5-carbethoxyaminophenol, 2-methoxy-5-carbethoxyaminophenol, 2-methyl-5-ureidophenol, 2,4-diaminophenoxyethanol, 2,4-diaminoanisole, 2,6-dimethyl-meta-phenylenediamine, (2-amino-4-N-methylaminophenoxy)-ethanol, 2,4-diaminophenyl β-methoxyethyl ether, 2,4-diaminophenyl β-mesylaminoethyl ether, 2-N-carbamylmethylamino-4-aminoanisole, 3-amino-4-methoxyphenol, α-naphthol, 2,6-diaminopyridine and 1-phenyl-3-methylpyrazol-5-one;

(2) ortho-phenylenediamines and ortho-aminophenols optionally containing substituents on the nucleus or on the amino groups, or ortho-diphenol, it being possible for these products to lead, by means of complex oxidation mechanisms, to new coloured compounds, either by cyclisation with themselves or by reacting with the para-phenylenediamines;

(3) dyestuff precursors of the benzene series, containing, on the nucleus, at least three substituents chosen from the group comprising hydroxyl, methoxy or amino groups, such as 2,6-diaminohydroquinone dihydrochloride, 2,6-diamino-4-N,N-bis-(ethyl)-aminophenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline;

(4) dyestuff precursors of the naphthalene series, such as 2-hydroxy-1,4-naphthoquinone and 5-hydroxy-1,4-naphthoquinone;

(5) leuco derivatives of indoanilines or of indophenols, such as 4,4'-dihydroxy-2-amino-5-methyldiphenylamine, 4,4'-dihydroxy-2-N-(β-hydroxyethyl)-amino-5-methyl-2'-chlorodiphenylamine, 2,4'-diamino-4-hydroxy-5-methyldiphenylamine, 2,4-dihydroxy-4'-N-(β-methoxyethyl)-aminodiphenylamine and 2,4-dihydroxy-5-methyl-4'-N-(β-methoxyethyl)-aminodiphenylamine;

(6) direct dyestuffs chosen from the nitro benzene dyestuffs, such as 1-N,N-bis-(β-hydroxyethyl)-amino-3-nitro-4-N'-methylaminobenzene, 1-[N-methyl-N-(β-hydroxyethyl)-amino]-3-nitro-4-N'-(β-hydroxyethyl)-aminobenzene, 1-[N-methyl-N-(β-hydroxyethyl)-amino]-3-nitro-4-N'-methylaminobenzene, 3-nitro-4-N-(β-hydroxyethyl)-aminoanisole, 3-nitro-4-N-(β-hydroxyethyl)-aminophenol, 3-nitro-4-aminophenoxyethanol, 3-nitro-4-(N-methylamino)-phenoxyethanol and 2-N-(β-hydroxyethyl)-amino-5-nitroanisole; and (7) various customary adjuvants, such as penetrating agents, foaming agents, thickeners, antioxidants, alkalising or acidifying agents, perfumes, sequestering agents and film-forming products.

The pH of the dyeing compositions according to the invention should be basic, for example from 8 to 11.5. Amongst the alkalising agents which can be used for this purpose, there may be mentioned ammonia, alkylamines, such as ethylamine or triethylamine, alkanolamines, such as mono- di- or tri-ethanolamine, alkylalkanolamines, such as methyldiethanolamine, sodium hydroxide or potassium hydroxide and sodium carbonate, potassium carbonate or ammonium carbonate. Amongst the acidifying agents which can be used, if necessary, there may be mentioned lactic acid, acetic acid, tartaric acid and phosphoric acid.

Anionic, cationic, non-ionic or amphoteric water-soluble surface-active agents can also be included in the composition according to the invention. Amongst the surface-active agents which can be used there may be mentioned, in particular, alkylbenzenesulphonates, alkylnaphthalenesulphonates, sulphates, ether-sulphates and sulphonates of fatty alcohols, quaternary ammonium salts, such as trimethylacetylammonium bromide and cetylpyridinium bromide, diethanolamides of fatty acids, and polyoxyethyleneated or polyglycerolated acids, alcohols or alkylphenols. The surface-active agents are preferably present in the composition according to the invention in a proportion of 0.5 to 55% by weight, and advantageously 4 to 40% by weight, relative to the total weight of the composition.

Organic solvents can also be included in the composition according to the invention in order to solubilise compounds which would not otherwise be sufficiently water-soluble. Amongst the solvents which can advantageously be used, examples which may be mentioned are ethanol, isopropanol, glycerol, glycols and their ethers, such as 2-butoxyethanol, ethylene glycol, propylene glycol and diethylene glycol monoethyl ether and monomethyl ether. The solvents are advantageously present in the composition in a proportion from 1 to 40% by weight, and preferably 5 to 30% by weight, relative to the total weight of the composition.

The thickening products which can be included in the composition according to the invention include sodium alginate, gum arabic, cellulose derivatives, such as methylcellulose, hydroxyethylcellulose, hydroxypropylmethylcellulose and the sodium salt of carboxymethylcellulose, and acrylic acid polymers; inorganic thickeners, such as bentonite, can also be used. The thickeners are preferably present in a proportion of 0.5 to 5% by weight, relative to the total weight of the composition, and advantageously 0.5 to 3% by weight.

The antioxidants which can be included in the composition according to the invention are advantageously sodium sulphite, thioglycolic acid, sodium bisulphite, ascorbic acid or hydroquinone. These antioxidants are suitably present in the composition in a proportion of 0.05 to 1.5% by weight, relative to the total weight of the composition.

At the time of use, the dyeing composition according to the invention contains oxidising agents, such as hydrogen peroxide, urea peroxide, or per-salts, such as ammonium persulphate.

In general, the meta-phenylenediamines of the formula (I) are present in the dyeing composition according to the invention in a proportion of 0.001 to 2.5% by weight, relative to the total weight of the composition.

The dyeing composition according to the invention can be presented in the form of, for example, a liquid, a cream, a gel or an aerosol or in any other form which is suitable for dyeing keratin fibres.

The present invention also provides a hair-dyeing process, characterised in that a dyeing composition of this invention is mixed, at the time of use, with a sufficient amount of an oxidising agent, in that the said mixture is left to act on the hair for say, 10 to 45 minutes, and in that the hair is rinsed, optionally washed and rinsed again, and dried.

The compounds of the formula (I) can be obtained by a process in which the nitro group of an acetylated compound of the formula:

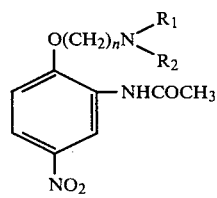

in which n, $R_1$ and $R_2$ have the meanings indicated above, is reduced and the product is then deacetylated by means of a hot acid treatment in order to obtain the product of the formula (I).

The following Examples further illustrate the present invention; Examples 1 and 2 illustrate the preparation of two meta-phenylenediamines of the formula (I).

EXAMPLE 1

Preparation of 2,4-diaminophenyl β-diethylaminoethyl ether trihydrochloride

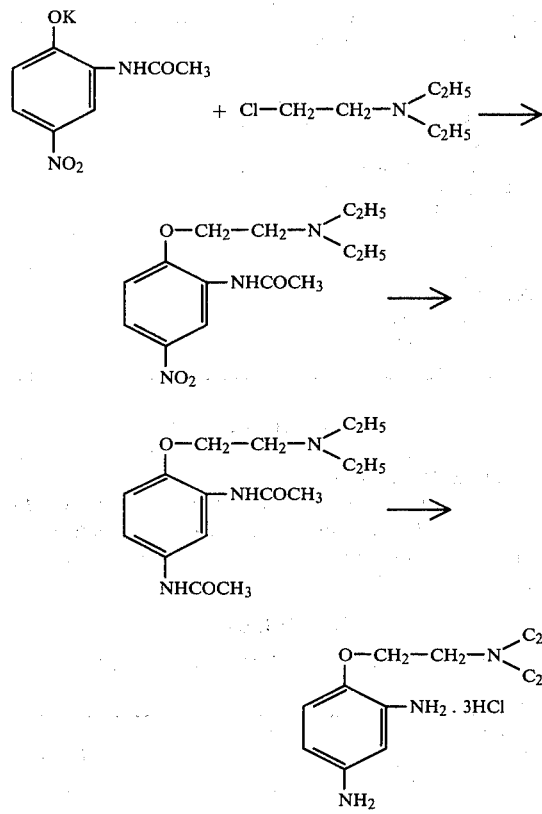

First step: Preparation of 2-acetylamino-4-nitrophenyl β-N,N-diethylaminoethyl ether 117 g (0.5 mol) of 2-acetylamino-4-nitrophenol, in the form of the potassium salt, are introduced into 350 ml of dimethylformamide and the mixture is then heated to 60° C., whilst stirring. 88.2 g (0.65 mol) of diethylaminoethyl chloride are then added; the reaction medium is heated at 95° C. for 150 minutes and is then poured into 1,500 ml of iced water; the expected product precipitates. This product is filtered off and washed with a 0.5 N sodium carbonate solution and then with water. After filtration, the product is finally dried in vacuo at 45° C. It melts at 117° C.

Analysis of the product obtained gives the following results:

| ANALYSIS | CALCULATED FOR $C_{14}H_{21}N_3O_4$ | FOUND |
|---|---|---|
| C % | 56.93 | 57.15 |
| H % | 7.17 | 7.47 |
| N % | 14.23 | 14.35 |

Second step: Preparation of 2,4-diacetylphenyl β-N,N-diethylaminoethyl ether 6 g of iron powder are added to 60 ml of water to which 1.6 ml of acetic acid have been added. The mixture is heated to 75° C. and 10 g (0.34 mol) of previously prepared 2-acetylamino-4-nitrophenyl β-diethylaminoethyl ether are then added gradually, whilst stirring. The reduction is exothermic and the mixture is heated under reflux. After having maintained reflux for 15 minutes, the reaction medium is neutralised with sodium carbonate and is then filtered at the boil, the filtrate being collected in 7 ml of acetic anhydride. After 30 minutes, ammonia is added until the pH reaches 9.2; the expected product which has precipitated is then filtered off. After washing with water, drying and recrystallisation from dioxane, the product melts at 155° C.

Third step: Preparation of 2,4-diaminophenyl β-diethylaminoethyl ether trihydrochloride 78 g (0.25 ml) of 2,4-diacetylphenyl β-N,N-diethylaminoethyl ether are introduced into 390 ml of ethanol which is saturated with hydrogen chloride and has been heated to 65° C. beforehand. The reaction medium is heated under reflux for 3 hours and the expected product, which has precipitated in the form of the trihydrochloride, is then filtered off. After washing with iced ethanol and drying in vacuo, the product melts above 260° C. with decomposition.

Analysis of the product obtained gives the following results:

| ANALYSIS | CALCULATED FOR $C_{12}H_{21}N_3O$ . 3HCl | FOUND |
|---|---|---|
| C % | 43.32 | 43.04 |
| H % | 7.27 | 6.90 |
| N % | 12.63 | 12.54 |
| Cl % | 31.97 | 31.80 |

EXAMPLE 2

Preparation of 2,4-diaminophenyl γ-N,N-dimethylaminopropyl ether trihydrochloride

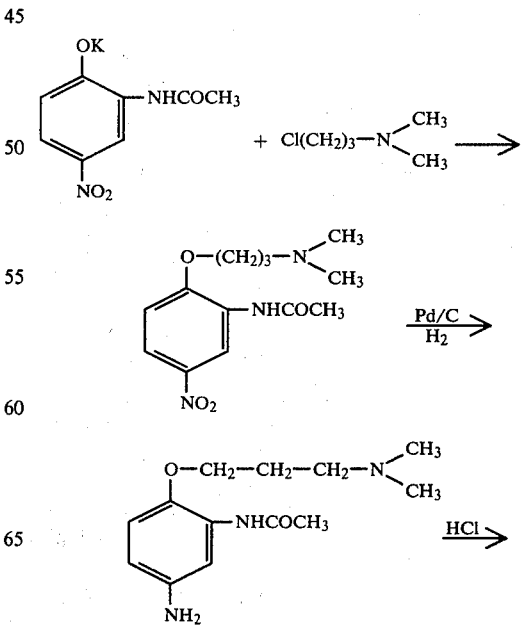

-continued

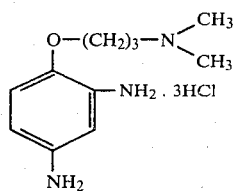

First step: Preparation of 2-acetylamino-4-nitrophenyl γ-N,N-dimethylaminopropyl ether 35.1 g (0.15 mol) of 2-acetylamino-4-nitrophenol, in the form of the potassium salt, are introduced into 105 ml of dimethylformamide and the mixture is then heated to 60° C., whilst stirring. 25.8 g (0.21 mol) of γ-dimethylaminopropyl chloride are then added; the reaction medium is heated at 90° C. for 210 minutes and is then poured into 750 g of iced water to which 40 ml of 1 N sodium hydroxide solution have been added. The expected product is extracted with methyl isobutyl ketone. After the methyl isobutyl ketone has been driven off in vacuo, the expected product is obtained in the form of an orange oil which crystallises rapidly (melting point: 69° C.).

The theoretical molecular weight calculated for $C_{13}H_{19}O_4N_3$ is 281. The weight found by potentiometric determination in acetic acid, using M/10 perchloric acid, is 283.

Analysis of the product obtained gives the following results:

| ANALYSIS | CALCULATED FOR $C_{13}H_{19}N_3O_4$ | FOUND |
|---|---|---|
| C % | 55.50 | 55.22 |
| H % | 6.81 | 7.08 |
| N % | 14.94 | 14.79 |

Second step: Preparation of 2-acetylamino-4-aminophenyl γ-N,N-dimethylaminopropyl ether 7 g of 2-acetylamino-4-nitrophenyl γ-N,N-dimethylaminopropyl ether are dissolved in 35 ml of absolute ethanol. 0.5 g of 10% strength palladium-on-charcoal is added as a catalyst and the reduction is carried out in a reaction bomb under a hydrogen pressure of 40 bars, at 60° C., for 30 minutes. After the catalyst has been removed by filtration, the alcohol is driven off in vacuo to give the expected product in the form of an oil, which will be used as such for the following step.

Third step: Preparation of 2,4-diaminophenyl γ-N,N-dimethylaminopropyl ether trihydrochloride 57 g of 2-acetylamino-4-aminophenyl γN,N-dimethylaminopropyl ether in 112 ml of hydrochloric acid (d=1.19) are heated for 75 minutes in a boiling water bath. The reaction medium is cooled and 75 ml of acetone are then added. The expected product precipitates in the form of the trihydrochloride, which melts at 236° C. with decomposition.

Analysis of the product obtained gives the following results:

| ANALYSIS | CALCULATED FOR $C_{11}H_9ON_3 \cdot 3HCl$ | FOUND |
|---|---|---|
| C % | 41.44 | 41.20 |
| H % | 6.91 | 7.07 |
| N % | 13.19 | 13.10 |
| Cl % | 33.44 | 33.50 |

EXAMPLE 3

The following dyeing composition is prepared:

| | |
|---|---|
| 2,4-Diaminophenyl β-diethylaminoethyl ether trihydrochloride | 0.184 g |
| Para-phenylenediamine | 0.06 g |
| Cetyl/stearyl alcohol sold under the name "ALFOL C16/18 E" by "CONDEA" | 8 g |
| Sodium cetyl-/stearyl-sulphate sold under the name "Lanette Wax E" by "HENKEL" | 0.5 g |
| Oxyethyleneated castor oil sold under the name "CEMULSOL B" by "RHONE POULENC" | 1 g |
| Oleyl diethanolamide | 1.5 g |
| The pentasodium salt of diethylenetriaminepentaacetic acid, sold under the name "MASQUOL DTPA" | 2.5 g |
| Ammonia solution (22° B strength) | 11 g |
| Water q.s.p. | 100 g |

The pH of the composition is equal to 11.

100 g of hydrogen peroxide of 20 volumes strength are added at the time of use.

When applied to 90% naturally white hair for 25 minutes at 28° C., this mixture imparts to the hair, after rinsing and shampooing, a bluish silver-grey colouration.

EXAMPLE 4

The following dyeing composition is prepared:

| | |
|---|---|
| N,N-Di-β-hydroxyethyl-para-phenylenediamine dihydrochloride | 2.69 g |
| 2,4-Diaminophenyl β-diethylaminoethyl ether trihydrochloride | 3.32 g |
| Nonylphenol containing four mols of ethylene oxide, sold under the name "CEMULSOL NP4" by "RHONE POULENC" | 21 g |
| Nonylphenol containing nine mols of ethylene oxide, sold under the name "CEMULSOL NP9" by "RHONE POULENC" | 24 g |
| Oleic acid | 4 g |
| 2-Butoxyethanol | 3 g |
| Ethanol (96° strength) | 10 g |
| The pentasodium salt of diethylenetriaminepentaacetic acid, sold under the name "MASQUOL DTPA" | 2.5 g |
| Thioglycolic acid | 0.6 g |
| Ammonia solution (22° B strength) | 10 g |
| Water q.s.p. | 100 g |

The pH of the composition is equal to 9.

100 g of hydrogen peroxide of 20 volumes strength are added at the time of use.

When applied to 90% naturally white hair for 15 minutes at 25° C., this mixture imparts to the hair, after rinsing and shampooing, an intense turquoise-blue colouration.

EXAMPLE 5

The following dyeing composition is prepared:

| | |
|---|---|
| N-β-Methoxyethyl-para-phenylenediamine dihydrochloride | 1.5 g |
| Para-aminophenol | 0.8 g |
| 2,4-Diaminophenyl β-diethylaminoethyl ether trihydrochloride | 0.8 g |
| 2-Methylresorcinol | 0.4 g |
| 2-Methyl-5-N-(β-hydroxyethyl)-aminophenol | 0.65 g |
| 6-Hydroxybenzomorpholine | 0.27 g |
| 2-Nitro-4-methyl-6-aminophenol | 1 g |
| Nonylphenol containing four mols of ethylene oxide, sold under the name "CEMULSOL NP4" by "RHONE POULENC" | 21 g |
| Nonylphenol containing nine mols of ethylene oxide, sold under the name "CEMULSOL NP9" by "RHONE POULENC" | 24 g |
| Oleic acid | 4 g |
| 2-Butoxyethanol | 3 g |
| Ethanol (96° strength) | 10 g |
| The pentasodium salt of diethylenetriamine-pentaacetic acid, sold under the name "MASQUOL DTPA" | 2.5 g |
| Thioglycolic acid | 0.6 g |
| Ammonia solution (22° B strength) | 10 g |
| Water q.s.p. | 100 g |

The pH of the composition is equal to 9.4.

85 g of hydrogen peroxide of 20 volumes strength are added at the time of use.

When applied to naturally very light chestnut hair for 35 minutes at 28° C., this mixture imparts to the hair, after rinsing and shampooing, a deep chestnut colouration.

EXAMPLE 6

The following dyeing composition is prepared:

| | |
|---|---|
| 2,4-Diaminophenyl β-diethylaminoethyl ether trihydrochloride | 0.09 g |
| 2,4-Diaminophenoxyethanol dihydrochloride | 0.06 g |
| 2,6-Dimethyl-5-acetylaminophenol | 0.48 g |
| 2,3-Dimethyl-para-phenylenediamine dihydrochloride | 0.15 g |
| Para-aminophenol | 0.5 g |
| N-Methyl-para-aminophenol sulphate | 0.3 g |
| 2-Amino-3-nitroisopropylbenzene | 0.5 g |
| Crosslinked polyacrylic acid sold under the name "CARBOPOL 934" by "GOODRICH CHEMICAL COMPANY" | 3 g |
| Ethanol (96° strength) | 11 g |
| 2-Butoxyethanol | 5 g |
| Trimethylcetylammonium bromide | 2 g |
| Ethylenediaminetetraacetic acid | 0.2 g |
| Ammonia solution (22° B strength) | 10 g |
| Sodium bisulphite solution (35° B strength) | 1 g |
| Water q.s.p. | 100 g |

The pH of the composition is equal to 9.4.

60 g of hydrogen peroxide of 20 volumes strength are added at the time of use.

When applied for 25 minutes at 25° C. to hair which has been bleached white, this mixture imparts to the hair, after rinsing and shampooing, a mahogany colouration.

EXAMPLE 7

The following dyeing composition is prepared:

| | |
|---|---|
| 2,4-Diaminophenyl β-diethylaminoethyl ether trihydrochloride | 0.03 g |
| Resorcinol | 0.83 g |
| Meta-aminophenol | 0.67 g |
| 2-Methyl-5-carbethoxyaminophenol | 0.1 g |
| Para-phenylenediamine | 0.85 g |
| Para-aminophenol | 0.63 g |
| 3-N-Methylamino-4-nitrophenoxyethanol | 0.2 g |
| Carboxymethylcellulose | 2 g |
| Ammonium lauryl-sulphate | 5 g |
| Ammonium acetate | 1 g |
| Propylene glycol | 8 g |
| The pentasodium salt of diethylenetriamine-pentaacetic acid, sold under the name "MASQUOL DTPA" | 2 g |
| Thioglycolic acid | 0.4 g |
| 2-Butoxyethanol | 8 g |
| Ammonia solution (22° B strength) | 4 g |
| Water q.s.p. | 100 g |

The pH of the composition is equal to 9.5.

70 g of hydrogen peroxide of 20 volumes strength are added at the time of use.

When applied to 90% naturally white hair for 20 minutes at 28° C., this mixture imparts to the hair, after rinsing and shampooing, a medium chestnut colouration with a golden sheen.

EXAMPLE 8

The following dyeing composition is prepared:

| | |
|---|---|
| 2,5-Diaminopyridine dihydrochloride | 0.9 g |
| 2,5-Diaminoisopropylbenzene dihydrochloride | 0.2 g |
| 2,4-Diaminophenyl β-diethylaminoethyl ether trihydrochloride | 0.4 g |
| Pyrocatechol | 0.2 g |
| 2-Methyl-5-aminophenol | 0.2 g |
| 1-Phenyl-3-methylpyrazol-5-one | 0.15 g |
| 3-Nitro-4-N-(β-hydroxyethyl)-aminophenol | 0.5 g |
| Nonylphenol containing four mols of ethylene oxide, sold under the name "CEMULSOL NP4" by "RHONE POULENC" | 12 g |
| Nonylphenol containing nine mols of ethylene oxide, sold under the name "CEMULSOL NP9" by "RHONE POULENC" | 15 g |
| Oxyethyleneated oleyl alcohol containing two mols of ethylene oxide | 1.5 g |
| Oxyethyleneated oleyl alcohol containing four mols of ethylene oxide | 1.5 g |
| Propylene glycol | 6 g |
| Ethylenediaminetetraacetic acid | 0.12 g |
| Ammonia solution (22° B strength) | 11 g |
| Thioglycolic acid | 0.6 g |
| Water q.s.p. | 100 g |

The pH of the composition is equal to 9.9.

100 g of hydrogen peroxide of 20 volumes strength are added at the time of use.

When applied to 90% naturally white hair for 20 minutes at 28° C., this mixture imparts to the hair, after rinsing and shampooing, a light mahogany colouration.

EXAMPLE 9

The following dyeing composition is prepared:

| | |
|---|---|
| 2,6-Dimethyl-para-phenylenediamine dihydrochloride | 1 g |
| N-Methyl-para-aminophenol sulphate | 0.3 g |
| 2,4-Diaminophenyl β-diethylaminoethyl ether trihydrochloride | 0.6 g |
| Resorcinol | 0.32 g |
| 2-Methyl-5-N-(β-hydroxyethyl)-aminophenol | 0.28 g |
| 2-Methyl-4-amino-5-nitrophenol | 0.7 g |
| Cetyl/stearyl alcohol sold under the name "ALFOL C16/18 E" by "CONDEA" | 8 g |
| Sodium cetyl-/stearyl-sulphate sold under | |

-continued

| | |
|---|---|
| the name "Lanette Wax E" by "HENKEL" | 0.5 g |
| Oxyethyleneated castor oil sold under the name "CEMULSOL B" by "RHONE POULENC" | 1 g |
| Oleyl diethanolamide | 1.5 g |
| The pentasodium salt of diethylenetriamine-pentaacetic acid, sold under the name "MASQUOL DTPA" | 2.5 g |
| Mercaptosuccinic acid | 0.35 g |
| Ammonia solution (22° B strength) | 11 g |
| Water q.s.p. | 100 g |

The pH of the composition is equal to 10.

80 g of hydrogen peroxide of 20 volumes strength are added at the time of use.

When applied to 90% naturally white hair for 25 minutes at 30° C., this mixture imparts to the hair, after rinsing and shampooing, a deep chestnut colouration.

EXAMPLE 10

The following dyeing composition is prepared:

| | |
|---|---|
| 2,4-Diaminophenyl β-diethylaminoethyl ether trihydrochloride | 0.35 g |
| Para-phenylenediamine | 0.2 g |
| Resorcinol | 0.35 g |
| Meta-aminophenol | 0.35 g |
| Para-aminophenol | 0.4 g |
| 3-Nitro-4-aminophenol | 0.6 g |
| Cetyl/stearyl alcohol sold under the name "ALFOL C16/18 E" by "CONDEA" | 8 g |
| Sodium cetyl-/stearyl-sulphate sold under the name "Lanette Wax E" by "HENKEL" | 0.5 g |
| Oxyethyleneated castor oil sold under the name "CEMULSOL B" by "RHONE POULENC" | 1 g |
| Oleyl diethanolamide | 1.5 g |
| The pentasodium salt of diethylenetriamine-pentaacetic acid, sold under the name "MASQUOL DTPA" | 2.5 g |
| Thioglycolic acid | 0.5 g |
| Hydroquinone | 0.15 g |
| Ammonia solution (22° B strength) | 11 g |
| Water q.s.p. | 100 g |

The pH of the composition is equal to 10.3.

100 g of hydrogen peroxide of 20 volumes strength are added at the time of use.

When applied to 90% naturally white hair for 30 minutes at 30° C., this mixture imparts to the hair, after rinsing and shampooing, a copper colouration.

EXAMPLE 11

The following dyeing composition is prepared:

| | |
|---|---|
| 2,4-Diaminophenyl β-diethylaminoethyl ether trihydrochloride | 0.21 g |
| 2-Methyl-5-N-(β-hydroxyethyl)-aminophenol | 0.22 g |
| 4-N,N-(β-Hydroxyethyl)-aminoaniline dihydrochloride | 2.71 g |
| Ortho-aminophenol | 0.39 g |
| Para-aminophenol | 0.234 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing twelve mols of ethylene oxide, sold under the name "ETHOMEEN TO12" | 4.5 g |
| Diethanolamides of copra fatty acids | 9 g |
| Propylene glycol | 4 g |
| 2-Butoxyethanol | 8 g |

-continued

| | |
|---|---|
| Ethanol (96° strength) | 6 g |
| The pentasodium salt of diethylenetriamine-pentaacetic acid, sold under the name "MASQUOL DTPA" | 2 g |
| Hydroquinone | 0.15 g |
| Sodium bisulphite solution (35° B strength) | 1.3 g |
| Ammonia solution (22° B strength) | 10 g |
| Water q.s.p. | 100 g |

The pH of the composition is equal to 9.7.

100 g of hydrogen peroxide of 20 volumes strength are added at the time of use.

When applied to 90% naturally white hair for 25 minutes at 28° C., this mixture imparts to the hair, after rinsing and shampooing, a fairly dark blue-grey colouration.

EXAMPLE 12

The following dyeing composition is prepared:

| | |
|---|---|
| 2,5-Diaminoisopropylbenzene dihydrochloride | 4.24 g |
| Para-aminophenol | 0.8 g |
| 2,4-Diaminophenyl β-diethylaminoethyl ether trihydrochloride | 2 g |
| 2-Methyl-5-N-(β-hydroxyethyl)-aminophenol | 0.5 g |
| Resorcinol | 0.8 g |
| Meta-aminophenol | 0.8 g |
| 1-Phenyl-3-methylpyrazol-5-one | 0.2 g |
| 2-Amino-3-nitrophenol | 1 g |
| Cetyl/stearyl alcohol sold under the name "ALFOL C16/18 E" by "CONDEA" | 8 g |
| Sodium cetyl-/stearyl-sulphate sold under the name "Lanette Wax E" by "HENKEL" | 0.5 g |
| Oxyethyleneated castor oil sold under the name "CEMULSOL B" by "RHONE POULENC" | 1 g |
| Oleyl diethanolamide | 1.5 g |
| The pentasodium salt of diethylenetriamine-pentaacetic acid, sold under the name "MASQUOL DTPA" | 2.5 g |
| Thioglycolic acid | 0.5 g |
| Hydroquinone | 0.15 g |
| Ammonia solution (22° B strength) | 11 g |
| Water q.s.p. | 100 g |

The pH of the composition is equal to 9.2.

100 g of hydrogen peroxide of 20 volumes strength are added at the time of use.

When applied for 25 minutes at 28° C. to hair which has been bleached straw blond, this mixture imparts to the hair, after rinsing and shampooing, a black colouration with a violet sheen.

EXAMPLE 13

The following dyeing composition is prepared:

| | |
|---|---|
| 2,4-Diaminophenyl β-diethylaminoethyl ether trihydrochloride | 0.11 g |
| Meta-aminophenol | 0.43 g |
| Resorcinol | 0.81 g |
| 2-Methyl-5-N-(β-hydroxyethyl)-aminophenol | 0.32 g |
| Para-phenylenediamine | 1 g |
| 2,3-Dimethyl-para-phenylenediamine dihydrochloride | 0.5 g |
| Ortho-aminophenol | 0.25 g |
| Nonylphenol containing four mols of ethylene oxide, sold under the name "CEMULSOL NP4" by "RHONE POULENC" | 21 g |
| Nonylphenol containing nine mols of ethylene oxide, sold under the name "CEMULSOL NP9" by "RHONE POULENC" | 24 g |
| Oleic acid | 4 g |

-continued

| | |
|---|---|
| 2-Butoxyethanol | 3 g |
| Ethanol (96° strength) | 10 g |
| The pentasodium salt of diethylenetriamine-pentaacetic acid, sold under the name "MASQUOL DTPA" | 2.5 g |
| Thioglycolic acid | 0.6 g |
| Ammonia solution (22° B strength) | 10 g |
| Water q.s.p. | 100 g |

The pH of the composition is equal to 10.3.

100 g of hydrogen peroxide of 20 volumes strength are added at the time of use.

When applied to 90% naturally white hair for 25 minutes at 25° C., this mixture imparts to the hair, after rinsing and shampooing, a brown colouration.

EXAMPLE 14

The following dyeing composition is prepared:

| | |
|---|---|
| 2,4-Diaminophenyl β-diethylaminoethyl ether trihydrochloride | 0.005 g |
| 2-Methyl-5-N-(β-hydroxyethyl)-aminophenol | 0.0013 g |
| 2,5-Diaminoisopropylbenzene dihydrochloride | 0.003 g |
| Carboxymethylcellulose | 2 g |
| Ammonium lauryl-sulphate | 5 g |
| Ammonium acetate | 1 g |
| Propylene glycol | 8 g |
| The pentasodium salt of diethylenetriamine-pentaacetic acid, sold under the name "MASQUOL DTPA" | 2 g |
| Thioglycolic acid | 0.4 g |
| 2-Butoxyethanol | 8 g |
| Triethanolamine | 0.6 g |
| Water q.s.p. | 100 g |

The pH of the composition is equal to 8.

20 g of hydrogen peroxide of 20 volumes strength are added at the time of use.

When applied for 35 minutes at 30° C. to hair which has been bleached light straw yellow, this mixture imparts to the hair, after rinsing and shampooing, a pearlescent appearance.

EXAMPLE 15

The following dyeing composition is prepared:

| | |
|---|---|
| 2,4-Diaminophenyl β-diethylaminoethyl ether trihydrochloride | 0.2 g |
| Meta-aminophenol | 0.2 g |
| 2-Methyl-5-N-carbethoxyaminophenol | 0.05 g |
| 4-[N-Ethyl-N-(β-hydroxyethyl)-amino]-aniline dihydrochloride | 0.4 g |
| Para-aminophenol | 0.155 g |
| 3-Nitro-4-N'-methylamino-N,N-(β-hydroxyethyl)-aniline | 1 g |
| 2-N-(β-Hydroxyethyl)-amino-5-nitro-phenoxyethanol | 0.2 g |
| Sodium lauryl-sulphate containing two mols of ethylene oxide | 20 g |
| Ethylenediaminetetraacetic acid | 0.2 g |
| Sodium bisulphite solution (35° B strength) | 1 g |
| Ammonia solution (22° B strength) | 10 g |
| Water q.s.p. | 100 g |

The pH of the composition is equal to 9.8.

70 g of hydrogen peroxide of 20 volumes strength are added at the time of use.

When applied to 90% naturally white hair for 25 minutes at 25° C., this mixture imparts to the hair, after rinsing and shampooing, a tin grey colouration.

EXAMPLE 16

The following dyeing compositon is prepared:

| | |
|---|---|
| 2,4-Diaminophenyl β-dimethylaminopropyl ether trihydrochloride | 1.5 g |
| Pyrocatechol | 0.52 g |
| 2,5-Diaminopyridine dihydrochloride | 1 g |
| Para-phenylenediamine | 0.6 g |
| Ortho-aminophenol | 0.53 g |
| Cetyl/stearyl alcohol sold under the name "ALFOL C16/18 E" by "CONDEA" | 8 g |
| Sodium cetyl-/stearyl-sulphate sold under the name "Lanette Wax E" by "HENKEL" | 0.5 g |
| Oxyethyleneated castor oil sold under the name "CEMULSOL B" by "RHONE POULENC" | 1 g |
| Oleyl diethanolamide | 1.5 g |
| The pentasodium salt of diethylenetriamine-pentaacetic acid, sold under the name "MASQUOL DTPA" | 2.5 g |
| Hydroquinone | 0.15 g |
| Thioglycolic acid | 0.5 g |
| Ammonia solution (22° B strength) | 11 g |
| Water q.s.p. | 100 g |

The pH of the composition is equal to 9.9.

100 g of hydrogen peroxide of 20 volumes strength are added at the time of use.

When applied to naturally light hair for 30 minutes at 28° C., this mixture imparts to the hair, after rinsing and shampooing, a dark brown colouration.

EXAMPLE 17

The following dyeing composition is prepared:

| | |
|---|---|
| 2,4-Diaminophenyl γ-dimethylaminopropyl ether trihydrochloride | 0.1 g |
| Resorcinol | 0.17 g |
| Meta-aminophenol | 0.055 g |
| 2,6-Dimethyl-5-acetylaminophenol | 0.15 g |
| 2,5-Diaminoisopropylbenzene dihydrochloride | 0.075 g |
| Para-aminophenol | 0.31 g |
| 2-Amino-3-nitroisopropylbenzene | 0.1 g |
| Crosslinked polyacrylic acid sold under the name "CARBOPOL 934" by "GOODRICH CHEMICAL COMPANY" | 3 g |
| Ethanol (96° strength) | 11 g |
| 2-Butoxyethanol | 5 g |
| Trimethylcetylammonium bromide | 2 g |
| Ethylenediaminetetraacetic acid | 0.2 g |
| Ammonia solution (22° B strength) | 10 g |
| Sodium bisulphite solution (35° B strength) | 1 g |
| Water q.s.p. | 100 g |

The pH of the composition is equal to 9.5.

90 g of hydrogen peroxide of 20 volumes strength are added at the time of use.

When applied for 20 minutes at 25° C. to hair which has been bleached white, this mixture imparts to the hair, after rinsing and shampooing, a golden blond colouration.

EXAMPLE 18

The following dyeing composition is prepared:

| | |
|---|---|
| 2,4-Diaminophenyl γ-dimethylaminopropyl ether trihydrochloride | 0.80 g |
| Para-aminophenol | 0.27 g |
| Sodium lauryl-sulphate containing two mols of ethylene oxide | 20 g |
| Ethylenediaminetetraacetic acid | 0.2 g |
| Sodium bisulphite solution (35° B strength) | 1 g |

-continued

| Ammonia solution (22° B strength) | 10 g |
| Water q.s.p. | 100 g |

The pH of the composition is equal to 10.3.

100 g of hydrogen peroxide of 20 volumes strength are added at the time of use.

When applied for 30 minutes at 25° C. to hair which has been bleached white, this mixture imparts to the hair, after rinsing and shampooing, a salmon pink colouration.

EXAMPLE 19

The following dyeing composition is prepared:

| 2,4-Diaminophenyl γ-dimethylaminopropyl ether trihydrochloride | 0.005 g |
| 2,4-Diaminophenoxyethanol dihydrochloride | 0.092 g |
| Resorcinol | 1.21 g |
| Meta-aminophenol | 0.71 g |
| Isopropyl-para-phenylenediamine dihydrochloride | 2.12 g |
| Para-aminophenol | 0.71 g |
| Nonylphenol containing four mols of ethylene oxide, sold under the name "CEMULSOL NP4" by "RHONE POULENC" | 12 g |
| Nonylphenol containing nine mols of ethylene oxide, sold under the name "CEMULSOL NP9" by "RHONE POULENC" | 15 g |
| Oxyethyleneated oleyl alcohol containing two mols of ethylene oxide | 1.5 g |
| Oxyethyleneated oleyl alcohol containing four mols of ethylene oxide | 1.5 g |
| Propylene glycol | 6 g |
| Ethylenediaminetetraacetic acid | 0.12 g |
| Ammonia solution (22° B strength) | 11 g |
| Thioglycolic acid | 0.6 g |
| Water q.s.p. | 100 g |

The pH of the composition is equal to 9.8.

100 g of hydrogen peroxide of 20 volumes strength are added at the time of use.

When applied to 90% naturally white hair for 30 minutes at 28° C., this mixture imparts to the hair, after rinsing and shampooing, a golden medium chestnut colouration.

We claim:

1. A composition suitable for dyeing keratin fibres which comprises, in an appropriate carrier, at least one oxidation base, and as the coupler, at least one compound of the formula (I):

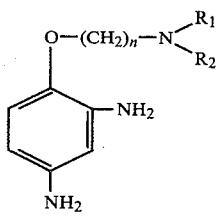

(I)

in which formula n is equal to 2, 3 or 4 and $R_1$ and $R_2$ are identical or different and represent an alkyl group having from 1 to 4 carbon atoms, or an acid salt thereof.

2. A composition according to claim 1, in which the compound of formula (I) is present in an amount from 0.001 to 2.5% by weight based on the total weight of the composition.

3. A composition according to claim 1 which has a pH of 8 to 11.5.

4. A composition according to claim 1, in which the oxidation base is a para-phenylenediamine, para-aminophenol or heterocyclic base.

5. A composition according to claim 4, which contains, as the oxidation base, at least one para-phenylenediamine of the general formula:

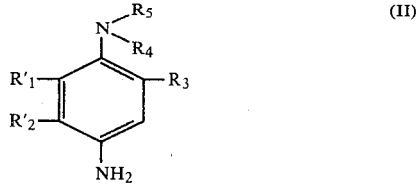

(II)

or an acid salt thereof, in which formula $R'_1$, $R'_2$ and $R_3$ are identical or different and represent a hydrogen atom, an alkyl radical having from 1 to 4 carbon atoms, an alkoxy radical having 1 or 2 carbon atoms, or a halogen atom, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamylalkyl, alkylsulphonamidoalkyl, acetylaminoalkyl, ureidoalkyl, carbethoxyaminoalkyl, aminoalkyl, monoalkylaminoalkyl, dialkylaminoalkyl, piperidinoalkyl or morpholinoalkyl radical, the alkyl groups in $R_4$ and $R_5$ having from 1 to 4 carbon atoms, or $R_4$ and $R_5$ form, together with the nitrogen atom to which they are attached, a piperidino or morpholino group, with the proviso that $R'_1$ and $R_3$ represent a hydrogen atom if $R_4$ and $R_5$ do not represent a hydrogen atom.

6. A composition according to claim 4, which contains, as the oxidation base, at least one para-aminophenol of the general formula:

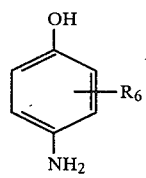

(III)

or an acid salt thereof, in which formula $R_6$ represents a hydrogen atom, an alkyl radical having from 1 to 4 carbon atoms, or a halogen atom.

7. A composition according to claim 4, which contains, as the oxidation base, at least one heterocyclic base which is 2,5-diaminopyridine, 3-methyl-7-aminobenzomorpholine or 5-aminoindole.

8. A composition according to claim 1, which contains at least one ortho-phenylenediamine or ortho-aminophenol, which is unsubstituted or substituted on the nucleus or on the amino group, or ortho-diphenol.

9. A composition according to claim 1, which contains 4,4'-dihydroxy-2-amino-5-methyldiphenylamine, 4,4'-dihydroxy-2-N-(β-hydroxyethyl)-amino-5-methyl-2'-chlorodiphenylamine, 2,4'-diamino-4-hydroxy-5-methyldiphenylamine, 2,4-dihydroxy-4'-N-(β-methoxyethyl)-aminodiphenylamine or 2,4-dihydroxy-5-methyl-4'-N-(β-methoxyethyl)-aminodiphenylamine.

10. A composition according to claim 1, which contains at least one nitrobenzene dyestuff.

11. A composition according to claim 1, which contains at least one dyestuff precursor of the naphthalene series.

12. A composition according to claim 1, which contains, in addition to a coupler of formula (I), at least one other coupler selected from resorcinol, pyrocatechol, 2-methylresorcinol, 2-ethylresorcinol, meta-aminophenol, 2-methyl-5aminophenol, 2-methyl-5-N-(β-hydroxyethyl)-aminophenol, 6-hydroxybenzomorpholine, 2,6-dimethyl-3-acetylaminophenol, 2-methyl-5-carbethoxyaminophenol, 2-methoxy-5-carbethoxyaminophenol, 2-methyl-5-ureidophenol, 2,4-diaminophenoxyethanol, 2,4-diaminoanisole, 2,6-dimethyl-meta-phenylenediamine, (2-amino-4-N-methylaminophenoxy)-ethanol, 2,4-diaminophenyl β-methoxyethyl ether, 2,4-diaminophenyl β-mesylaminoethyl ether, 2-N-carbamylmethylamino-4-aminoanisole, 3-amino-4-methoxyphenol, α-naphthol, 2,6-diaminopyridine and 1-phenyl-3-methylpyrazol-5-one.

13. A composition according to claim 1 which contains at least one dyestuff precursor of the benzene series, which contains, on the nucleus, at least three substituents which are hydroxyl, methoxy or amino groups.

14. A composition according to claim 13, in which the dyestuff precursor of the benzene series is selected from 2,6-diaminohydroquinone dihydrochloride, 2,6-diamino-4-N,N-bis-(ethyl)-aminophenol trihydrochloride, 2,4-diaminophenol dihydrochloride, 1,2,4-trihydroxybenzene, 2,3,5-trihydroxytoluene and 4-methoxy-2-amino-N-(β-hydroxyethyl)-aniline.

15. A composition according to claim 1, which contains at least one penetrating agent, foaming agent, thickener, antioxidant, alkalising or acidifying agent, perfume, sequestering agent or film-forming product.

16. A composition according to claim 15, in which the alkalising agent is ammonia, an alkylamine, alkanolamine or alkylalkanolamine, sodium hydroxide or potassium hydroxide or sodium carbonate, potassium carbonate or ammonium carbonate, and the acidifying agent is lactic, acetic, tartaric or phosphoric acid.

17. A composition according to claim 1 which contains, based on the total weight of the composition, from 0.5 to 55% by weight of one or more surface-active agents selected from an alkylbenzenesulphonate, alkylnaphthalenesulphonate, sulphate, ether-sulphate or sulphonate of a fatty alcohol, a quaternary ammonium salt, a diethanolamide of a fatty acid or a polyoxyethyleneated or polyglycerolated acid, alcohol or alkylphenol.

18. A composition according to claim 1, which contains, based on the total weight of the composition, from 1 to 40% by weight of one or more organic solvents selected from ethanol, isopropanol, glycerol, a glycol or glycol ether.

19. A composition according to claim 18, in which the organic solvent is ethylene glycol, propylene glycol, 2-butoxyethanol or diethylene glycol monoethyl ether and monomethyl ether.

20. A composition according to claim 1, which contains, based on the total weight of the composition, from 0.5 to 5% by weight of thickener selected from sodium alginate, gum arabic, cellulose derivative, an acrylic acid polymer and bentonite.

21. A composition according to claim 1, which contains, based on the total weight of the composition, from 0.05 to 1.5% by weight of antioxidant selected from sodium sulphite, thioglycolic acid, sodium bisulphite, ascorbic acid and hydroquinone.

22. A composition according to claim 1, which contains at least one oxidising agent selected from hydrogen peroxide, urea peroxide and a per-salt.

23. A composition according to claim 1, in which the compound of formula (I) is 2,4-diaminophenyl β-diethylaminoethyl ether or the trihydrochloride thereof.

24. A composition according to claim 1 for application to human hair.

25. A process for dyeing hair which comprises mixing, at the time of use, a composition as defined in claim 1 with an oxidising agent, if said composition does not already contain an oxidising agent, allowing the resulting mixture to act on the hair for 10 to 45 minutes, rinsing the hair, optionally washing and rinsing it again, and then drying the hair.

* * * * *